US011767620B2

(12) United States Patent
Sloan et al.

(10) Patent No.: US 11,767,620 B2
(45) Date of Patent: Sep. 26, 2023

(54) BRAIDED CORD WITH CHANGING CROSS-SECTIONAL AREA

(71) Applicant: KURARAY CO., LTD., Kurashiki (JP)

(72) Inventors: Forrest Sloan, Houston, TX (US); Patrick Coffey, Houston, TX (US)

(73) Assignee: KURARAY CO., LTD., Kurashiki (JP)

( * ) Notice: Subject to any disclaimer, the term of this patent is extended or adjusted under 35 U.S.C. 154(b) by 114 days.

(21) Appl. No.: 17/409,965

(22) Filed: Aug. 24, 2021

(65) Prior Publication Data

US 2022/0056622 A1 Feb. 24, 2022

Related U.S. Application Data

(60) Provisional application No. 63/069,182, filed on Aug. 24, 2020.

(51) Int. Cl.
*D04C 1/12* (2006.01)
*D07B 1/04* (2006.01)
*A61B 17/06* (2006.01)

(52) U.S. Cl.
CPC .............. *D04C 1/12* (2013.01); *D07B 1/04* (2013.01); *A61B 17/06166* (2013.01);
(Continued)

(58) Field of Classification Search
CPC .... D04C 1/12; D07B 1/04; D07B 2201/1024; D07B 2201/1096; D07B 2201/2026;
(Continued)

(56) References Cited

U.S. PATENT DOCUMENTS

| 1,786,936 A | 12/1930 | Craig |
| 5,019,093 A | 5/1991 | Kaplan et al. |

(Continued)

FOREIGN PATENT DOCUMENTS

| EP | 3458138 A1 | 3/2019 |
| JP | 4647299 B2 | 3/2011 |

(Continued)

OTHER PUBLICATIONS

International Search Report and Written Opinion dated Jan. 13, 2022 in PCT/US2021/047225, 16 pages.

*Primary Examiner* — Shaun R Hurley
(74) *Attorney, Agent, or Firm* — Element IP, PLC

(57) ABSTRACT

This application describes a braided cord containing a braided sheath and optionally a core surrounded by the braided sheath. The braided cord has changing cross-sectional area ranging from 0.0004 $mm^2$ to 30 $mm^2$ and contains one or more sections having a tapering angle ranging from 1° to 60° when observed in one direction along the cord axis. The change in the cross-sectional area of the cord can be achieved by changing the thickness of the braided sheath and/or changing the cross-sectional area of the core when the core is present. The thickness of the braided sheath can be adjusted by changing the size and/or twist level of one or more sheath strands, changing the pick count of the braided sheath, and/or using one or more shaped sheath strands. This application also describes a process of producing the braided cord with changing cross-sectional area.

21 Claims, 7 Drawing Sheets

(52) U.S. Cl.
CPC ................ *D07B 2201/1024* (2013.01); *D07B 2201/1096* (2013.01); *D07B 2201/209* (2013.01); *D07B 2201/2026* (2013.01); *D10B 2509/04* (2013.01)

(58) Field of Classification Search
CPC .............. D07B 2201/209; D02G 3/448; A61B 17/06166; D10B 2509/04
See application file for complete search history.

(56) References Cited

U.S. PATENT DOCUMENTS

| | | | |
|---|---|---|---|
| 5,217,495 | A | 6/1993 | Kaplan et al. |
| 5,261,886 | A | 11/1993 | Chesterfield et al. |
| 6,045,571 | A | 4/2000 | Hill et al. |
| 6,716,234 | B2 | 4/2004 | Grafton et al. |
| 6,841,214 | B1 | 1/2005 | Keith et al. |
| 8,079,973 | B2 | 12/2011 | Herrig |
| 8,182,466 | B2 | 5/2012 | Stehr et al. |
| 8,881,635 | B2 | 11/2014 | Martin |
| 9,125,659 | B2 | 9/2015 | Berez et al. |
| 2003/0050666 | A1 | 3/2003 | Grafton |
| 2004/0158312 | A1 | 8/2004 | Chouinard et al. |
| 2007/0213770 | A1 | 9/2007 | Dreyfuss |
| 2008/0097401 | A1* | 4/2008 | Trapp ................ D04C 1/06 604/527 |
| 2009/0158563 | A1 | 6/2009 | Nakanishi |
| 2012/0232655 | A1* | 9/2012 | Lorrison ................ D03D 3/02 28/151 |
| 2013/0255045 | A1 | 10/2013 | Gonzalez |
| 2014/0013931 | A1 | 1/2014 | Dow et al. |
| 2019/0133747 | A1* | 5/2019 | Janardhan ........ A61B 17/22031 |
| 2020/0022701 | A1* | 1/2020 | Crook .................. D04C 1/12 |

FOREIGN PATENT DOCUMENTS

| | | |
|---|---|---|
| JP | 5256211 B2 | 8/2013 |
| JP | 5318073 B2 | 10/2013 |
| JP | 5492792 B2 | 5/2014 |
| JP | 2018043086 A | 3/2018 |
| WO | WO-2017142874 A3 | 8/1917 |
| WO | WO-2008036156 A1 | 3/2008 |
| WO | WO-2017142874 A2 | 8/2017 |
| WO | WO-2019069817 A1 | 4/2019 |
| WO | WO-2019147460 A1 | 8/2019 |
| WO | WO-2020018773 A1 | 1/2020 |

* cited by examiner

BRAIDED CORD WITH CHANGING CROSS-SECTIONAL AREA

TECHNICAL FIELD

This application relates to braided cords having a braided sheath and optionally a core surrounded by the braided sheath. More specifically, it relates to fine braided cords with changing cross-sectional area and the preparation thereof. The braided cords disclosed herein can be used to make, for example, sutures and other medical cords for medical devices and instruments, such as tapered catheters, actuation cables, and device delivery systems. The braided cords disclosed herein can also be used in other industries to make, for example, fishing lines and nets.

BACKGROUND OF THE INVENTION

Medical cords are used in a variety of medical applications including surgical sutures, ligatures, artificial tendons and ligaments, tissue scaffolds, woven or knitted surgical meshes, and reinforced components in medical composites. Medical cords are usually constructed of tubular braid. The braided cords, in addition to the braided sheath, can have a core to maintain certain cross-sectional shape and required strength.

In many surgical procedures, it is desirable to use sutures that not only have excellent tensile strength and good knot-tying and knot-holding characteristics but also can be easily loaded onto various surgical instruments, some of which have very small openings. In some cases, it is ideal that the suture has a smooth surface to reduce tissue drag; while in some other cases, it is ideal that the suture has a textured surface to properly pinch or hold and to prevent movement of the suture after completion of the surgical procedure.

In addition, as medical instruments are inserted into the body of a patient, the pathways for reaching the intended target sites can become smaller and smaller. Therefore, medical cords that are reinforced with high-strength and low-elongation fibers and are designed to taper (gradually reduce in diameter) along the length would facilitate the production of such medical instruments.

Accordingly, it is an object of this application to provide a fine braided cord that has changing cross-sectional area to fulfil the above-needed applications. It is also an object of this application to provide an effective method to produce such cords.

SUMMARY OF THE DISCLOSURE

All ranges or lists of upper and lower values described throughout this description include all values (including the endpoints unless otherwise stated) and sub-ranges therein.

The use of "a" or "an" to describe various elements and components is only for convenience and to give a general sense of the disclosure. Such terms should be read to include one or more elements and components unless it is clear that it is otherwise intended. The terms "about" and "approximately" as used herein refer to being nearly the same as a referenced amount or value and should be understood to encompass ±5% of the specified amount or value. The term "substantially" as used herein, unless otherwise defined, means all or almost all or the vast majority, as would be understood by a person of ordinary skill in the art. It is intended to take into account some reasonable variance from 100% that would ordinarily occur in industrial-scale or commercial-scale situations.

Throughout this description, the term "fiber" includes monofilament fiber and multifilament fiber. The term "strand" includes mono-fiber strand and a strand of two or more fibers. The term "twist level" of a strand refers to the number of turns per unit length of a strand when the fibers in the strand is gathered by twisting. The term "size" of a strand refers to the number of fibers contained in the strand. The term "pick count" of a braided structure refers to the number of crossovers of strands per unit length of the braided axis, which is parallel to the longitudinal axis of a cord.

Unless otherwise defined or described, technical terms and methods employed to determine associated measurement values are in accordance with the description of ASTM D855/D885M-10A (2014), Standard Test Methods for Tire Cords, Tire Cord Fabrics, and Industrial Filament Yarns Made From Man-made Organic-base Fibers, published October 2014.

This application describes a braided cord that comprises a braided sheath of sheath strands braided along the longitudinal cord axis and optionally comprises a core surrounded by the braided sheath. The braided cord is a cord with changing cross-sectional area and contains one or more sections having a tapering angle ranging from 1° to 60° when observed in one direction along the cord axis. The cross-sectional area of the braided cord ranges from 0.0004 $mm^2$ to 30 $mm^2$. The cross-sectional area of the braided cord changes at a cross sectional area changing rate of larger than 1% per millimeter.

The change in the cross-sectional area of the braided cord can be achieved by changing the thickness of the braided sheath and/or changing the cross-sectional area of the core when a core is present. The thickness of the braided sheath can be adjusted by changing the size of one or more sheath strands, changing the twist level of one or more sheath strands, changing the pick count of the braided sheath, and/or using one or more shaped sheath strands, which is an untwisted strand having a twist level of less than 1 turn per meter, a cross-sectional aspect ratio of at least 3:1, and changing strand width.

The thus obtained braided cord can have one tapering end, two tapering ends, and/or an in-between section that has periodic or random cross-sectional area variation so that the in-between section contains one or more protrusions and/or depressions.

This application also describes a process of producing such braided cords.

The foregoing paragraphs have been provided by way of general introduction and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

The inventive braided cord contains a braided sheath of sheath strands braided along the cord axis and has changing cross-sectional area ranging from about 0.0004 mm² to about 30 mm². The cross section of the braided cord can be of various shapes. In the case where the braided cord is a round cord with a circular cross section, the diameter of the round braided cord may range from approximately 0.023 mm to approximately 6 mm. The portion of the braided cord where the cross-sectional area changes can be characterized by a tapering angle (θ), which ranges from about 1° to about 60° when observed in one direction along the cord axis. The tapering angle can be controlled depending on particular applications. In some embodiments, the tapering angle θ ranges from 5° to 45°, or from 10° to 30°. The cord can be coreless or further contains a core surrounded by the braided sheath.

Figure 1:
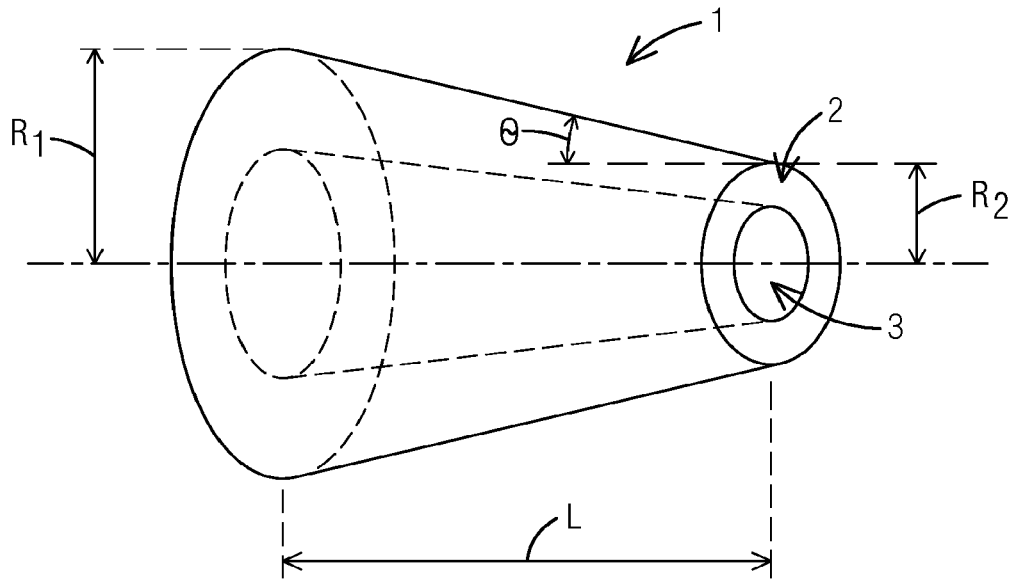
FIG. 1 schematically shows the calculation of the cross-sectional area changing rate of the inventive braided cord.

In addition to the tapering angle θ, the change of the cross-sectional area of the inventive braided cord can be characterized by a cross-sectional area changing rate of larger than 1% per millimeter. Depending on particular applications, the cross-sectional area changing rate can be larger than 10% per millimeter, or larger than 20% per millimeter. As schematically shown in FIG. 1, for an exemplified round cord 1 having a circular cross-sectional area with a sheath 2 and a core 3 (only a tapering portion of the cord 1 having a tapering angle θ is shown in the figure), the cross-sectional area changing rate (ACR) after tapering can be calculated as $$ACR = \frac{\pi R_1^2 - \pi R_2^2}{\pi R_1^2 \times L},$$

where $R_1$ is the radius of the cord before tapering, $R_2$ is the radius of the cord after tapering, and L is the tapering distance along the cord axis. Because $$L = \frac{R_1 - R_2}{\tan\theta},$$

ACR can be simplified as $$ACR = \frac{R_1 + R_2}{R_1^2} \tan\theta.$$

For example, the cross-sectional area changing rates for a section of a cord having various combinations of tapering angle θ, $R_1$, and $R_2$ are summarized in Table 1.

TABLE 1

| θ (°) | $R_1$ (mm) | $R_2$ (mm) | ACR (%/mm) |
|---|---|---|---|
| 1 | 2 | 0.5 | 1.1 |
| 5 | 2 | 0.5 | 5.5 |
| 15 | 2 | 0.5 | 16.7 |
| 30 | 2 | 0.5 | 36.1 |
| 45 | 2 | 0.5 | 62.5 |
| 60 | 2 | 1 | 130 |
| 60 | 2 | 0.5 | 108.3 |
| 60 | 2 | 0.25 | 97.4 |
| 60 | 1 | 0.5 | 260 |
| 60 | 0.5 | 0.25 | 520 |
| 60 | 3 | 0.02 | 58 |

The number of strands contained in the braided sheath depends upon particular requirements of the braided cord and the capabilities of the braiding device. It can range from 3 to more than 200 depending upon the particular application. In some embodiments it may range from 4 to 95, and in other applications it is limited to about 24. In medical applications, the number of strands in the braided sheath often ranges from 3 to 24.

The pick count of the braided sheath ranges from about 6 to about 3000 unit crossovers per linear meter of the braided cord. In other embodiments, the pick count of the braided sheath may range from about 15 to about 2000 unit crossovers per meter, or from about 20 to 1000 unit crossovers per meter.

The number of fibers (which can be monofilament fibers and/or multifilament fibers) contained in each sheath strand typically ranges from 1 to 10, preferably from 1 to 5, and more preferably from 1 to 3. A multifilament fiber typically contains filaments in the range of 2 to 600, preferably 5 to 80, and more preferably 5 to 20. The filaments in the sheath strands have linear density ranging from 0.2 denier to 30 denier, preferably from 2.5 denier to 20 denier, and more preferably from 5 denier to 10 denier.

Changing the thickness of the braided sheath is one way to obtain the inventive braided cord with changing cross-sectional area. If the braided cord has a core, changing the cross-sectional area of the core can be used alone or in combination with changing the thickness of the sheath to obtain the braided cord with changing cross-sectional area.

Figure 2A:
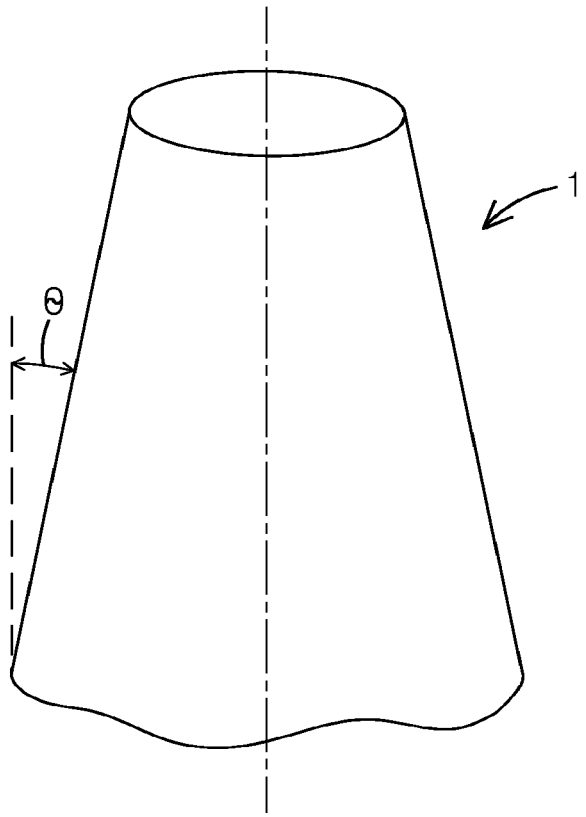
FIGS. 2A-2E schematically illustrate various embodiments of the inventive braided cord with changing cross-sectional area.
Figure 2B:
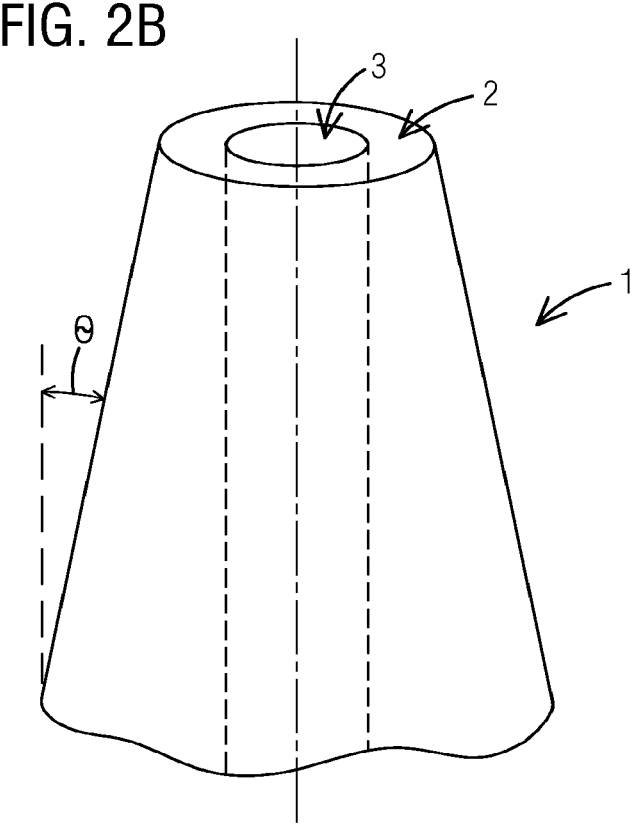
Figure 2C:
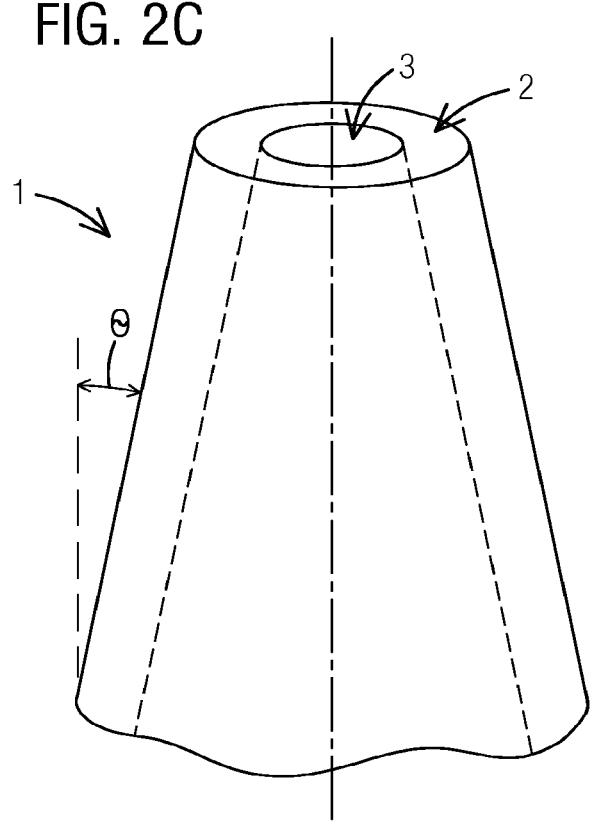
Figure 2D:
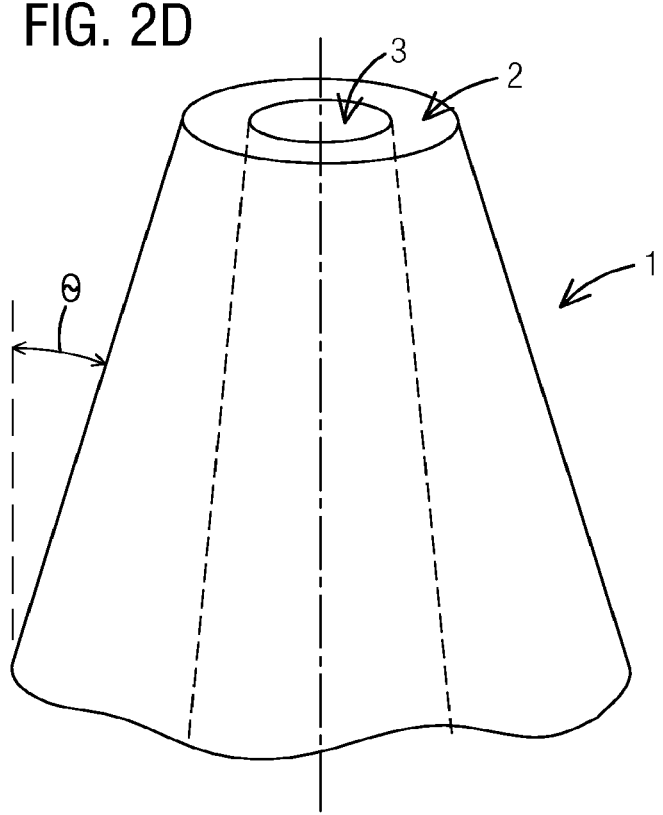
Figure 2E:
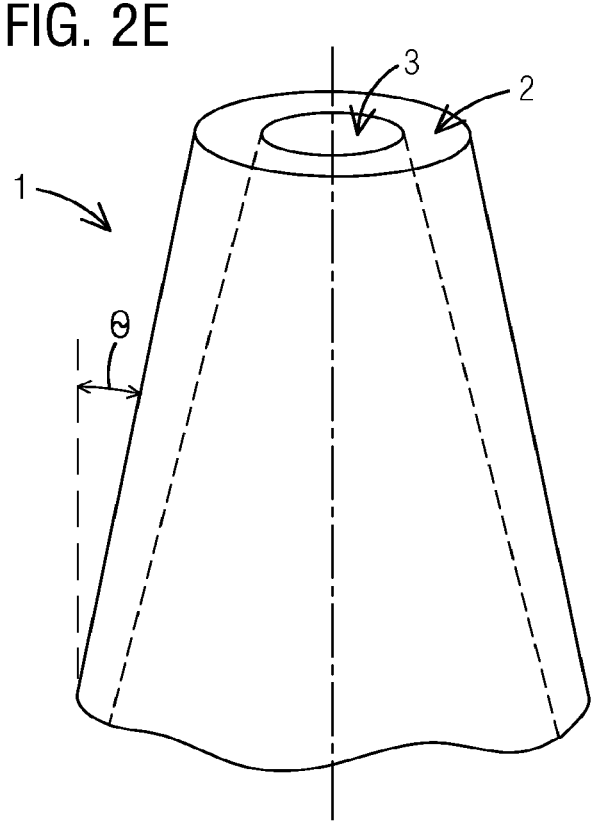

FIGS. 2A-2E schematically show various embodiments of the inventive braided cord with changing cross-sectional area (as characterized by a tapering angle θ). In particular, FIG. 2A shows a portion of a coreless braid cord 1 having a braided sheath with changing thickness. FIG. 2B shows a portion of a braided cord 1 having a braided sheath 2 with changing thickness and a core 3 with constant cross-sectional area. FIG. 2C shows a portion of a braided cord 1 having a braided sheath 2 with constant thickness and a core 3 with changing cross-sectional area. FIGS. 2D and 2E both show a portion of a braided cord 1 having both a braided sheath 2 with changing thickness and a core 3 with changing cross-sectional area. However, FIG. 2D differs from FIG. 2E in that the braided cord shown in FIG. 2D has a change in the cross-sectional area more rapid than that shown in FIG. 2E. Specifically, in FIG. 2D, the decreasing in the cross-sectional area of the core is in the same direction as the decreasing in the thickness of the braided sheath. In contrast, in FIG. 2E, the decreasing in the cross-sectional area of the core is mitigated by the increasing in the thickness of the braided sheath.

Several approaches are available to vary the thickness of the braided sheath. These approaches can be used alone or can be used in any combination to impart a more gradual or a more rapid change in the thickness of the braided sheath.

One approach is to change the strand size of the sheath strand(s) by reducing or adding the number of fibers contained in the sheath strand(s). For example, for a braid initially constructed from twelve (3×100d) strands (i.e., each strand is formed of 3 fibers and each fiber has a linear density of 100 denier), as the length of the braid increases, individual fiber(s) can be allowed to run out resulting in reduction in the thickness of the sheath, which may in turn lead to reduction in the overall cross-sectional area of the cord.

Another approach is to change the twist level of the sheath strand. Lengths of strands could be prepared with varying twist level, which could be marked in some fashion as twist level increased or decreased. Using these strands in the braided sheath would create the change in thickness, as higher twist tends to create more rounded cross sections with aspect ratio approaching 1.0.

Another approach is to change the pick count of the braided sheath. For example, gradually decreasing the pick count as braiding progressed can make the braided sheath thinner.

Figure 3:
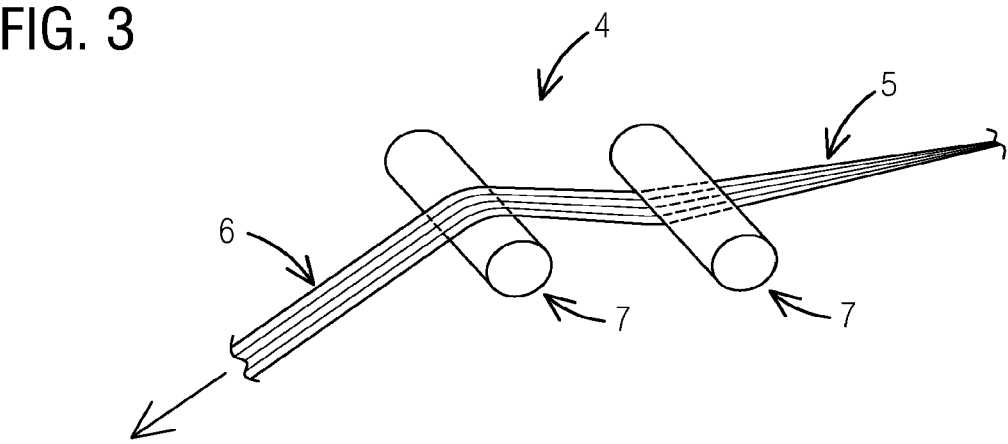
FIG. 3 schematically shows an exemplified shaping device that can be used in preparing a shaped strand for the inventive braided cord.

Another approach is to use one or more shaped strands, which are untwisted strands (i.e., strands with a twist level of less than 1 turn per meter), during braiding. As the braiding progresses, the one or more untwisted strands can be shaped by, for example, adjusting the tension applied to the strand(s) so that the shaped strand(s) are flattened in a controlled manner to change the strand width, thereby adjusting the thickness of the braided sheath. The shaped strands typically have a cross-sectional aspect ratio of at least 3:1. An example of the shaping device that can be used to prepare the shaped strands is shown in FIG. 3. In particular, the shaping device 4 includes rollers 7 and shapes the strand 5 to obtain the shaped strand 6. Methods and devices that can be used to prepare shaped strands are described in Provisional Patent Application No. 63/044,418, filed Jun. 26, 2020, entitled "Braided Jackets with Low Thickness," by Forrest Sloan et al. The disclosure of this provisional patent application is incorporated by reference herein in its entirety.

In addition, different braid patterns (e.g., tubular braid vs. flat braid) also lead to different thickness of the braided structure. Therefore, it is possible to further adjust the thickness of the braided sheath by changing braid patterns.

In the case where the braided cord has a core, the core can be a braided core, a knitted core, a twisted core, or a plied core. A core strand may be a mono-fiber strand or may comprise a plurality of fibers; and each fiber comprises one or more filaments having linear density ranging from 0.2 denier to 30 denier. A braided core may have a pick count ranging from about 6 to about 3000 unit crossovers per linear meter, or about 15 to about 2000 unit crossovers per meter, or from about 20 to 1000 unit crossovers per meter.

Figure 4A:
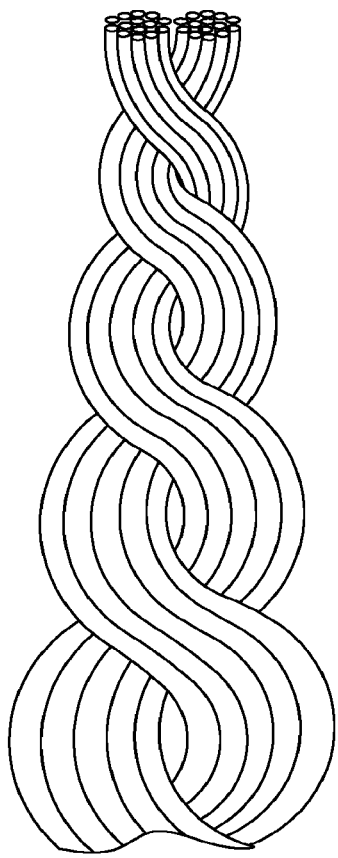
FIGS. 4A and 4B schematically illustrate embodiments of a core with changing cross-sectional area.
Figure 4B:
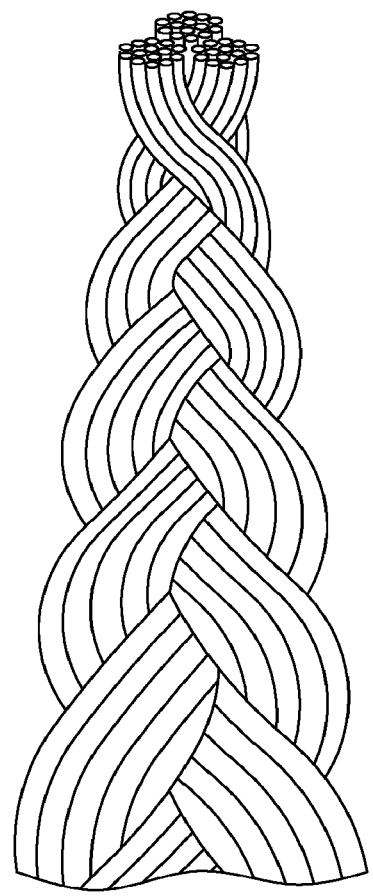

Exemplified cores with changing cross-sectional area are shown in FIGS. 4A and 4B. In particular, FIG. 4A shows a twisted 2-strand core with changing cross-sectional area; and FIG. 4B shows a braided 3-strand core with changing cross-sectional area.

Approaches similar to those making the braided sheath with changing thickness can be used to prepare a core with changing cross-sectional area. That is, the core with changing cross-sectional area can be prepared either by using core strand(s) having changing size; or by using core strands with varying twist levels (individually or collectively); or by changing pick counts of the core strands; or by using shaped strand(s) with changing strand width; or by any combination thereof.

For a braided cord having both a braided sheath and a core surrounded by the braided sheath, the approaches to make a braided sheath with changing thickness and the approaches to make a core with changing cross-sectional area can be combined in various manners so that the obtained braided cord not only has changing cross-sectional area but also may have various configurations and/or surface textures.

Figure 5:
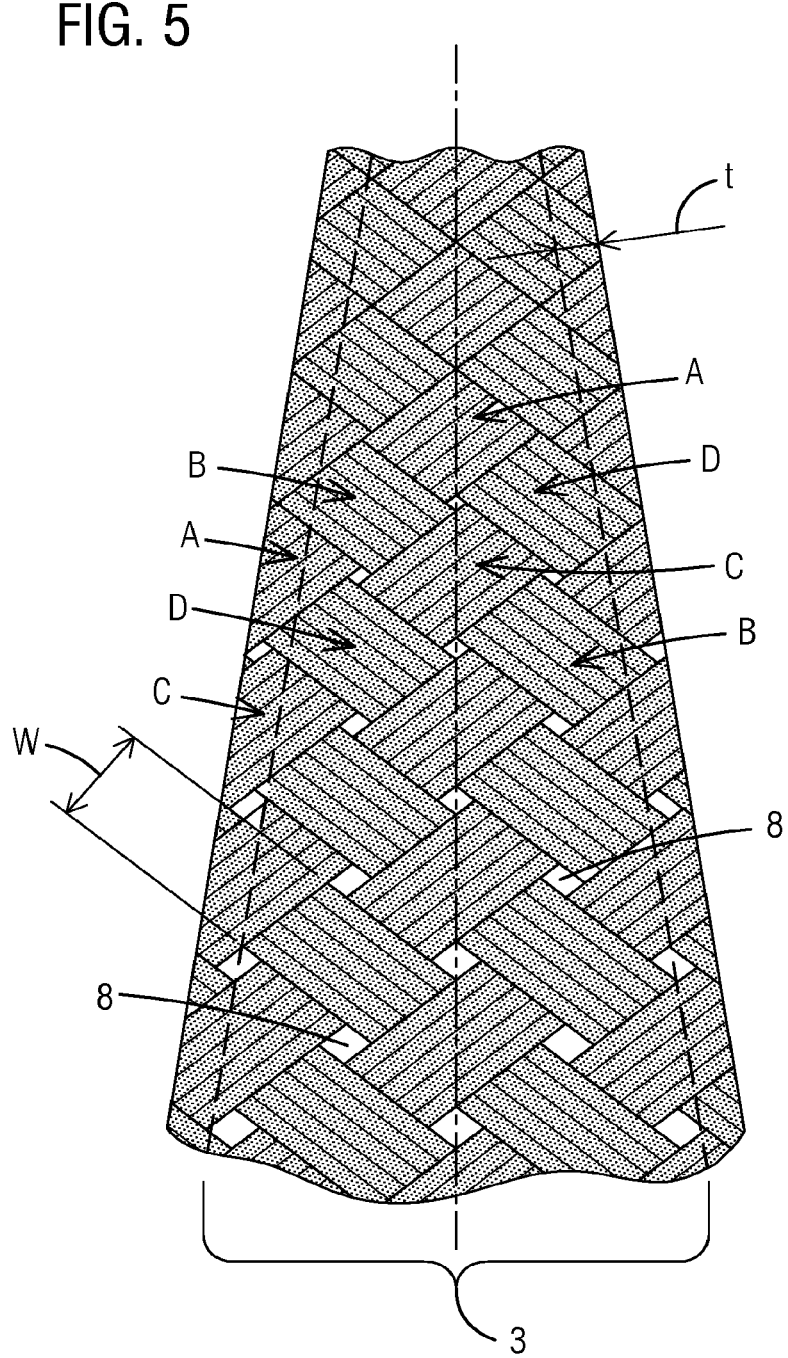
FIG. 5 schematically illustrates a braided cord having growing coverage gaps as the diameter of the cord increases.

For example, FIG. 5 illustrates a braided cord having a tapering core 3 and a 4-strand (strands A, B, C, and D) braided sheath with a constant thickness t. In this example, the sheath strands have no change in the aspect ratio; and thus, there is no change in the strand width w. In addition, the sheath is braided without changing the pick count or the strand size. As a result, although the portion of the core having a small diameter may be fully covered by the braided sheath, coverage gaps 8 appear as the diameter of the core increases. Creating coverage gaps could be advantageous for specific applications in order to, for example, achieve certain visual effect or provide gripping points.

Figure 6:
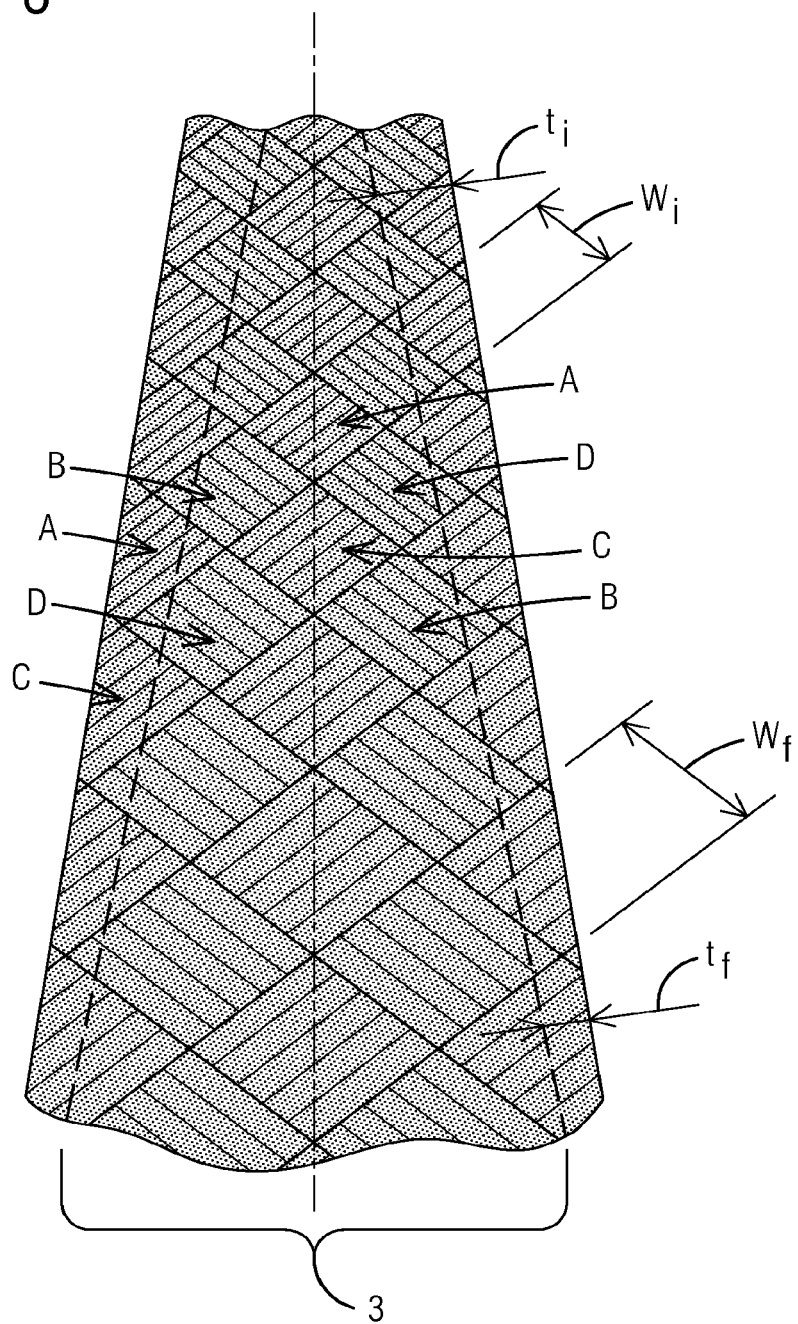
FIG. 6 schematically shows a braided cord without gaps in coverage as the diameter of the cord increases.

FIG. 6 shows a contrasting braided cord with a tapering core 3 and a 4-strand (strands A, B, C, and D) braided sheath with a changing thickness. In this example, shaping during braiding is used to prepare the braided sheath so that as the diameter of the core increases, the thickness of the sheath decreases ($t_i > t_f$), while the stand width increases ($w_i < w_f$). As a result, even if the sheath strands may be braided without changing the pick count, the core, no matter whether it is a portion having a small diameter or a portion having a large diameter, can be fully covered by the braided sheath without gaps. Accordingly, the braided cord shown in FIG. 6 would be expected to have a smoother surface than the braided cord shown in FIG. 5.

Figure 7A:
FIGS. 7A-7C schematically illustrate further embodiments of the inventive braided cord.
Figure 7B:

The braided cord described in this application can be a cord with one taping end, as schematically shown in FIG. 7A. It can also be a cord with two tapering ends, as schematically shown in FIG. 7B. A braided cord with one tapering end or two tapering ends can be used as surgical sutures for easy loading onto the surgical instruments with small openings.

Figure 7C:
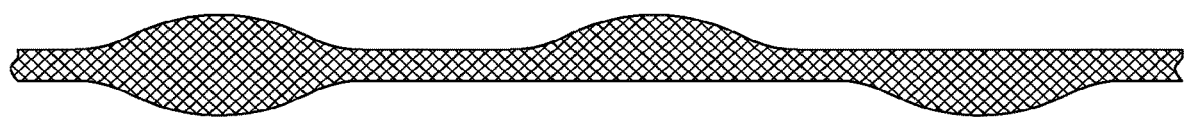

Further, the braided cord described in this application can be a cord with an in-between section that has periodic or random cross-sectional area variations so that the in-between section contains one or more protrusions and/or depressions, as schematically shown in FIG. 7C. Such cords thus can have a textured surface with tailored surface roughness and can be used, for example, as a suture that can pinch or hold to prevent movement of the suture.

The braided cord described in this application may be made of strands that are initially identical in size, structure, and filament composition, or may differ in any or all of size, structure, and filament composition.

The chemical composition of the filaments used to make the braided cord described in this application may be of any high performance polymer known to provide a combination of desired properties, such as tensile strength, tenacity, and creep characteristics. The filaments may be liquid crystalline polymer (LCP) filaments and/or non-LCP filaments. Exemplary filaments include liquid crystalline polyester filaments, aramid filaments, co-polymer aramid filaments, polyether ether ketone (PEEK) filaments, poly(p-phenylene benzobisoxazole) (PBO) filaments, ultra-high molecular weight polyethylene filaments, high modulus polyethylene filaments, polypropylene filaments, polyethylene terephthalate filaments, polyamide filaments, high-strength polyvinyl alcohol filaments, polyhydroquinone diimidazopyridine (PIPD) filaments, and any combination thereof.

The filaments contained in the braided sheath preferably include at least one of a liquid crystalline polyester filament, an aramid filament, co-polymer aramid filament, a PEEK filament, a PBO filament, an ultra-high molecular weight polyethylene filament, a high modulus polyethylene filament, a polypropylene filament, a polyethylene terephthalate filament, a polyamide filament, a PIPD filament, and a high-strength polyvinyl alcohol filament.

In the case where the braided cord has a core, the filaments contained in the core preferably include at least one of a liquid crystalline polyester filament, an aramid filament, co-polymer aramid filament, a PEEK filament, a PBO filament, an ultra-high molecular weight polyethylene filament, a polypropylene filament, a high modulus polyethylene filament, a polyethylene terephthalate filament, a polyamide filament, a PIPD filament, and a high-strength polyvinyl alcohol filament.

Exemplary polymerized units of the filaments are shown in Table 2. In the table, the number of Y substituent groups is equal to the maximum number of substitutable positions in the ring structure, and each Y independently represents a hydrogen atom, a halogen atom (for example, a fluorine atom, a chlorine atom, a bromine atom, and an iodine atom), an alkyl group (for example, an alkyl group having 1 to 4 carbon atoms such as a methyl group, an ethyl group, an isopropyl group, and a t-butyl group), an alkoxy group (for example, a methoxy group, an ethoxy group, an isopropoxy group, and an n-butoxy group), an aryl group (for example, a phenyl group and a naphthyl group), an aralkyl group (for example, a benzyl group and a phenethyl group), an aryloxy group (for example, a phenoxy group), an aralkyloxy group (for example, a benzyloxy group), or any mixture thereof

TABLE 2

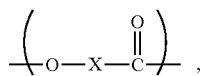

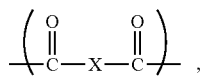

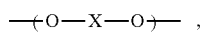

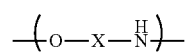

(in which X in the formulas is selected from the following structures)

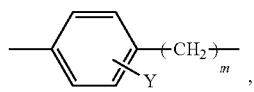

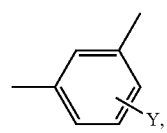

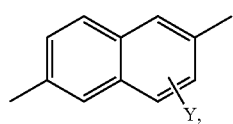

TABLE 2-continued

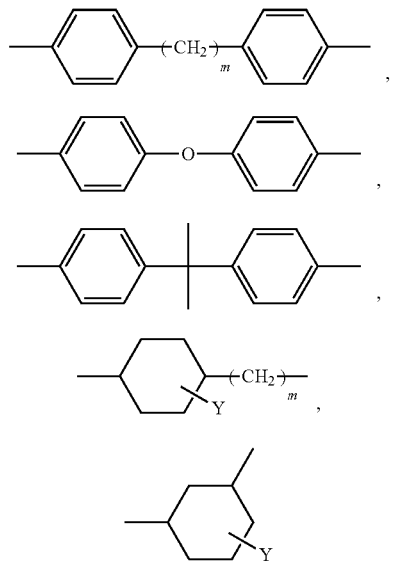

(in which m = 0 to 2, and Y = a substituent selected from a hydrogen atom, a halogen atom, an alkyl group, an aryl group, an aralkyl group, an alkoxy group, an aryloxy group, and an aralkyloxy group)

More specific polymerized units are illustrated in the structures shown in Tables 3-5 below. When the polymerized unit in the formulae is a unit which can represent plural structures, two or more units may be used in combination as polymerized units constituting a polymer.

TABLE 3

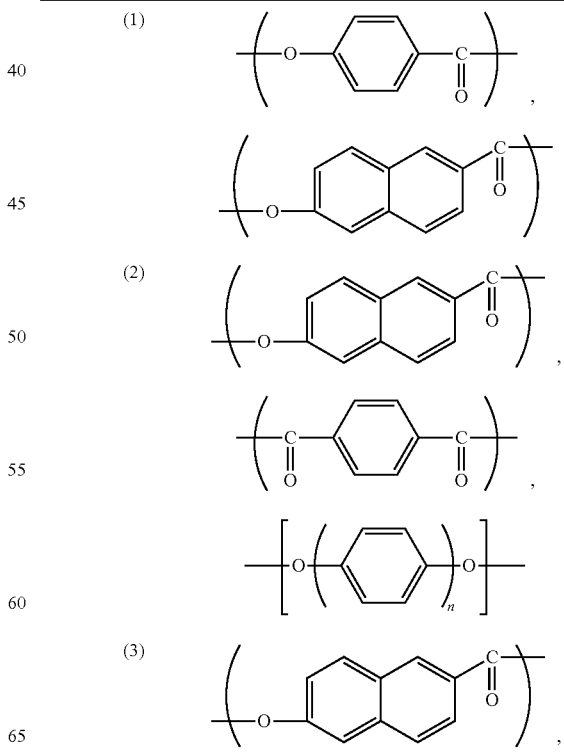

TABLE 3-continued
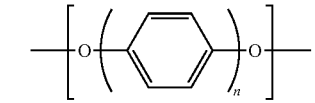

TABLE 4-continued
(10) 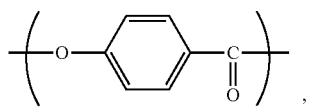
(11) 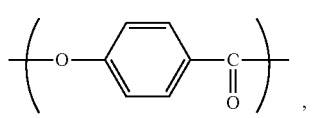
(12) 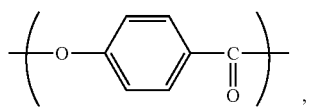
(13) 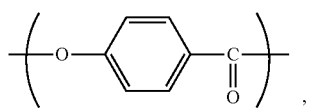
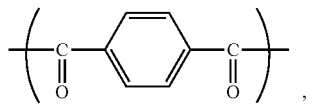
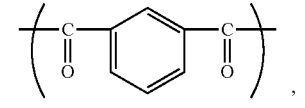
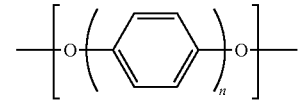
TABLE 4-continued
(14) 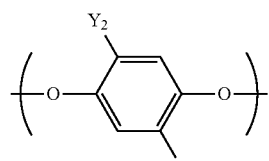
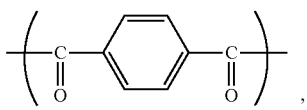
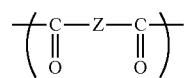
(15) 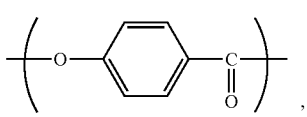
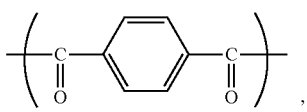
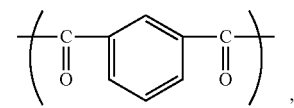
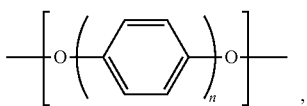
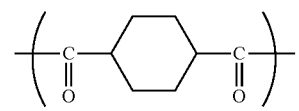
TABLE 5
(16) 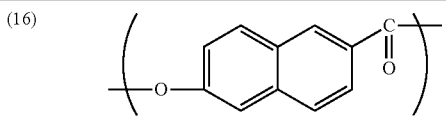
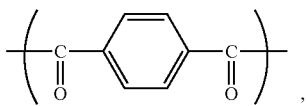
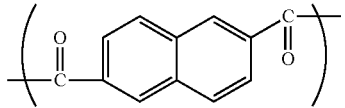
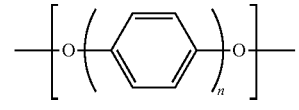

TABLE 5-continued

(17)
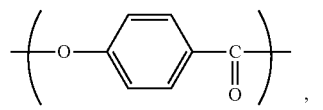,
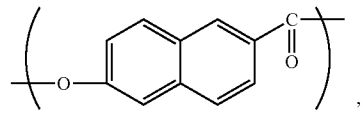,
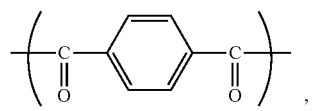,
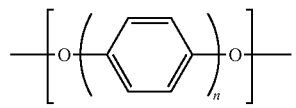

(18)
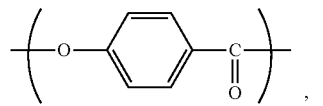,
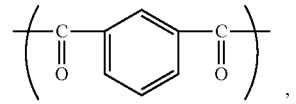,
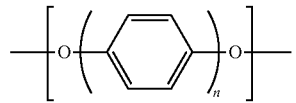

In the polymerized units of Tables 3, 4, and 5, n is an integer of 1 or 2, and the respective units n=1, n=2 may exist alone or in combination; and Y1 and Y2 each independently may be a hydrogen atom, a halogen atom (for example, a fluorine atom, a chlorine atom, a bromine atom, and an iodine atom), an alkyl group (for example, an alkyl group having 1 to 4 carbon atoms such as a methyl group, an ethyl group, an isopropyl group, and a t-butyl group), an alkoxy group (for example, a methoxy group, an ethoxy group, an isopropoxy group, and an n-butoxy group), an aryl group (for example, a phenyl group and a naphthyl group), an aralkyl group (for example, a benzyl group and a phenethyl group), an aryloxy group (for example, a phenoxy group), an aralkyloxy group (for example, a benzyloxy group), or any mixture thereof. Among these groups, Y is preferably a hydrogen atom, a chlorine atom, a bromine atom, or a methyl group.

Z in specie (14) of Table 4 may comprise divalent groups represented by the formulae below.

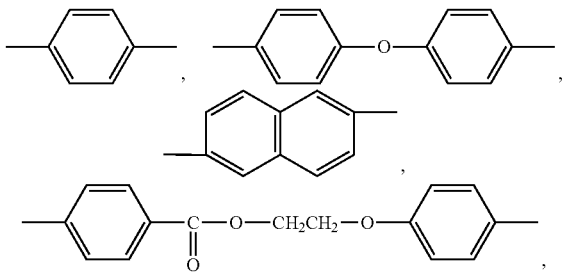

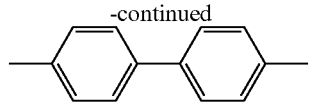

In some embodiments a liquid crystalline polyester may be a combination comprising a naphthalene skeleton as a polymerized unit. Particularly, it may include both a polymerized unit (A) derived from hydroxybenzoic acid and a polymerized unit (B) derived from hydroxynaphthoic acid. For example, the unit (A) may be of formula (A) and the unit (B) may be of formula (B). From the viewpoint of improving melt moldability, a ratio of the units (A) to the units (B) may be in the range of from 9/1 to 1/1, preferably 7/1 to 1/1, and more preferably 5/1 to 1/1.

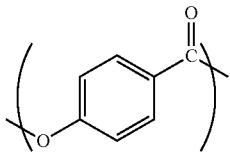 (A)

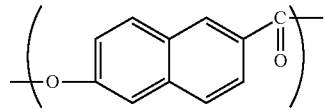 (B)

The total of the polymerized units (A) and the polymerized units (B) may be, for example, about 65 mol % or more, or about 70 mol % or more, or about 80 mol % or more, based on the total polymerized units. In some embodiments the braided sheath may include a liquid crystalline polyester comprising about 4 to about 45 mol % of the polymerized unit (B) in the polymer.

A melting point of the liquid crystalline polyester may be in the range of from about 250° C., or about 260° C., to about 360° C., or to about 320° C. The melting point as used herein is a main absorption peak temperature which is measured and observed by a differential scanning calorimeter (DSC) (e.g., "TA3000" manufactured by METTLER Co.) in accordance with the JIS K7121 test method. Specifically, 10 to 20 mg of a sample is used in the above-mentioned DSC apparatus and, after the sample is encapsulated in an aluminum pan, nitrogen is allowed to flow as a carrier gas at a flow rate of 100 cc/minute and an endothermic peak upon heating at a rate of 20° C./minute is measured. When a well-defined peak does not appear at the first run in the DSC measurement depending on the type of the polymer, the temperature is raised to a temperature which is 50° C. higher than an expected flow temperature at a temperature rise rate (or heating rate) of 50° C./minute, followed by complete melting at the same temperature for 3 minutes and further cooling to 50° C. at a temperature drop rate (or cooling rate) of −80° C./minute. Thereafter, the endothermic peak may be measured at a temperature rise rate of 20° C./minute.

Commercially available LCPs contained in the braided cords of the present disclosure may include VECTRAN® HT BLACK manufactured by KURARAY CO., LTD., VECTRAN® HT manufactured by KURARAY CO., LTD., SIVERAS® manufactured by Toray Industries, Inc., monofilament manufactured by ZEUS, and ZXION® manufactured by KB SEIREN, LTD.

Liquid crystalline polyester fibers in the present application may be obtained by melt spinning of a liquid crystalline polyester resin. The spun fiber may be further heat treated to enhance mechanical properties. The liquid crystalline polyester may be composed of a repeating polymerized unit, for example, derived from an aromatic diol, an aromatic dicarboxylic acid, or an aromatic hydroxycarboxylic acid. The liquid crystalline polyester may optionally further comprise a polymerized unit derived from an aromatic diamine, an aromatic hydroxyamine, and/or an aromatic aminocarboxylic acid.

Aramid fiber in the present application means a polyamide fiber with high heat resistance and high strength comprising a molecular skeleton composed of an aromatic (benzene) ring. Aramid fibers may be classified into a para-aramid fiber and a meta-aramid fiber according to a chemical structure thereof, with para-aramid fibers being preferably included in some braided sheaths of the present disclosure.

Examples of commercially available aramid fibers include para-aramid fibers, for example, KEVLAR® manufactured by E.I. du Pont de Nemours and Company, HERACRON® from Kolon Industries Inc., and TWARON® and TECHNORA® (copolyparaphenylene/3,4'-oxydiphenylene terephthalamide) manufactured by Teijin Limited; and meta-aramid fibers, for example, NOMEX® manufactured by E.I. du Pont de Nemours and Company and CONEX® manufactured by Teijin Limited.

Polyhydroquinone diimidazopyridine (PIPD) fibers (known as M5 fibers available from DuPont) are based on polymers of the following repeating unit:

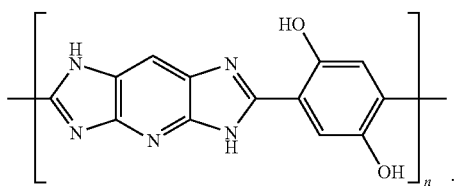

Polyparaphenylenebenzobisoxazole (poly(p-phenylene-2,6-benzobisoxazole) (PBO) fibers are commercially available as ZYLON® AS and ZYLON® HM manufactured by TOYOBO CO., LTD.

Ultra-high molecular weight polyethylene fibers in the braided cord of the present disclosure may have an intrinsic viscosity in the range of from about 5.0 dL/g, or from about 7.0 dL/g, or from about 10 dL/g, to about 30 dL/g, or to about 28 dL/g, or to about 24 dL/g. When the intrinsic viscosity of the ultra-high molecular weight polyethylene fiber is in the range of from about 5.0 dL/g to about 30 dL/g, fibers having good dimensional stability are obtained.

A weight average molecular weight of the ultra-high molecular weight polyethylene fiber may be from about 700,000, or from about 800,000, or from about 900,000, to about 8,000,000, or to about 7,000,000, or to about 6,000,000. When the weight average molecular weight of the ultra-high molecular weight polyethylene fiber is in the range of from about 700,000 to about 8,000,000, high tensile strength and elastic modulus may be obtained.

Due to difficulties in determining the weight average molecular weight of ultra-high molecular weight polyethylene fibers using GPC methods, it is possible to determine the weight average molecular weight based on a value of the above mentioned intrinsic viscosity according to the equation below mentioned in "Polymer Handbook Fourth Edition, Chapter 4 (John Wiley, published 1999)": Weight average molecular weight=$5.365 \times 10^4 \times$(intrinsic viscosity)$^{1.37}$.

In some embodiments, it may be preferable for the repeating units of an ultra-high molecular weight polyethylene fiber to contain substantially ethylene. However, it may be possible to use, in addition to a homopolymer of ethylene, a copolymer of ethylene with a small amount of another monomer, for example, α-olefin, acrylic acid and derivatives thereof, methacrylic acid and derivatives thereof, and vinylsilane and derivatives thereof. The polyethylene fiber may have a partial crosslinked structure. The polyethylene fiber may also be a blend of a high-density polyethylene with an ultra-high molecular weight polyethylene, a blend of a low-density polyethylene with an ultra-high molecular weight polyethylene, or a blend of a high-density polyethylene, a low-density polyethylene with an ultra-high molecular weight polyethylene. The polyethylene fiber may be a combination of two or more ultra-high molecular weight polyethylenes having different weight average molecular weights, or two or more polyethylenes having different molecular weight distributions.

Commercially available ultra-high molecular weight polyethylene fibers include DYNEEMA® SK60, DYNEEMA® SK, IZANAS® SK60, and IZANAS® SK71 manufactured by TOYOBO CO., LTD.; and SPECTRA FIBER 900® and SPECTRA FIBER 1000 manufactured by Honeywell, Ltd.

Filaments made of synthetic resins such as polyolefin-based, polyamide-based, and polyvinyl alcohol-based resins have good drawability. Structures, such as fibers and strands, made of such filaments thus can be smoothly and gradually tapered by feeding the material to a drawing apparatus and adjusting the drawing speed relative to the feeding speed. Such filaments may be especially preferred to prepare a smoothly tapered core for the braided cord described in this application.

In some embodiments, additional agents, such as coating compositions, may be added to the filaments, fibers, and/or strands of the braided cord described in this application to improve properties such as surface lubricity, abrasion resistance, water absorption resistance, and handleability. Exemplary coating compositions include cross-linked or non-crosslinked silicon polymers and long chain fatty acids.

The braided cord described in this application may also be colored using methods known in the art. For example, the braided cord may contain one or more colored strands, which may be produced by passing the strands through a colorant solution and then drying the color-coated strands at a high temperature. Inorganic colorants, such as titanium oxide and cadmium compounds, and organic colorants, such as azo compounds and cyanine dyes, may be used.

The above-described approaches to prepare a braided sheath with changing thickness and to prepare a core (when present) with changing cross-sectional area can be used in various combinations to prepare the inventive braided cord with changing cross-sectional area. By adjusting parameters (such as strand size, twist level, pick count, tensioning applied to the strand, and braid patterns) during processing, various braided cord with different configuration and textures can be prepared.

EMBODIMENTS

Embodiment [1] of the present disclosure relates to a braided cord, comprising:
- a braided sheath of sheath strands braided along a cord axis, and
- optionally a core surrounded by the braided sheath, wherein each sheath strand comprises one or more fibers and each fiber comprises one or more filaments; and
wherein
- with the proviso that the braided cord is coreless or has a core optionally with changing cross-sectional area, the braided sheath has changing thickness achieved by at least one mode selected from the group consisting of (i) one or more sheath strands having changing size, (ii) one or more sheath strands having changing twist level, (iii) the braided sheath having changing pick count, and (iv) the braided sheath comprising at least one shaped sheath strand, which is an untwisted strand having a twist level of less than 1 turn per meter, a cross-sectional aspect ratio of at least 3:1, and changing strand width; or
- with the proviso that the braided sheath has a constant thickness, the braided cord has a core with changing cross-sectional area so that the braided cord has changing cross-sectional area ranging from 0.0004 $mm^2$ to 30 $mm^2$ and contains one or more sections having a tapering angle ranging from 1° to 60° when observed in one direction along the cord axis.

Embodiment [2] of the present disclosure relates to the braided cord of Embodiment [1], wherein the tapering angle ranges from 5° to 45°.

Embodiment [3] of the present disclosure relates to the braided cord of Embodiments [1] and [2], wherein the cross-sectional area of the braided cord changes at a cross sectional area changing rate of larger than 1% per millimeter.

Embodiment [4] of the present disclosure relates to the braided cord of Embodiments [1]-[3], which is a cord with one tapering end.

Embodiment [5] of the present disclosure relates to the braided cord of Embodiments [1]-[3], which is a cord with two tapering ends.

Embodiment [6] of the present disclosure relates to the braided cord of Embodiments [1]-[5], wherein between two ends of the cord, the cord contains an in-between section that has periodic or random cross-sectional area variation so that the in-between section contains one or more protrusions and/or depressions.

Embodiment [7] of the present disclosure relates to the braided cord of Embodiments [1]-[6], wherein the braided sheath has a pick count ranging from 6 to 3000 unit crossovers per linear meter of the braided cord.

Embodiment [8] of the present disclosure relates to the braided cord of Embodiments [1]-[7], wherein the filaments in the sheath strands have linear density ranging from 0.2 denier to 30 denier.

Embodiment [9] of the present disclosure relates to the braided cord of Embodiments [1]-[8], wherein the braided sheath has changing thickness achieved by the braided sheath comprising one or more sheath strands having changing twist level.

Embodiment [10] of the present disclosure relates to the braided cord of Embodiments [1]-[9], wherein the braided sheath has changing thickness achieved by the braided sheath having changing pick count.

Embodiment [11] of the present disclosure relates to the braided cord of Embodiments [1]-[10], wherein the braided sheath has changing thickness achieved by the braided sheath comprising at least one shaped sheath strand, which is an untwisted strand having a twist level of less than 1 turn per meter, a cross-sectional aspect ratio of at least 3:1, and changing strand width.

Embodiment [12] of the present disclosure relates to the braided cord of Embodiments [1]-[11], wherein the braided cord is a coreless cord.

Embodiment [13] of the present disclosure relates to the braided cord of Embodiments [1]-[11], wherein the braided cord comprises the core surrounded by the braided sheath.

Embodiment [14] of the present disclosure relates to the braided cord of Embodiment [13], wherein the core is a braided core, a knitted core, a twisted core, or a plied core.

Embodiment [15] of the present disclosure relates to the braided cord of Embodiments [13] and [14], wherein the core is a braided core that comprises core strands braided along the cord axis.

Embodiment [16] of the present disclosure relates to the braided cord of Embodiment [15], wherein the braided core has a pick count ranging from 6 to 3000 unit crossovers per linear meter of the braided cord.

Embodiment [17] of the present disclosure relates to the braided cord of Embodiments [15] and [16], wherein the braided core has changing pick count so that the braided core has changing cross-sectional area.

Embodiment [18] of the present disclosure relates to the braided cord of Embodiments [13] and [14], wherein the core has changing cross-sectional area and is a twisted or braided core comprising a plurality of core strands.

Embodiment [19] of the present disclosure relates to the braided cord of Embodiment [18], wherein each core strand comprises one or more fibers and each fiber comprises one or more filaments having linear density ranging from 0.2 denier to 30 denier.

Embodiment [20] of the present disclosure relates to the braided cord of Embodiments [18] and [19], wherein the twisted or braided core comprises one or more core strands having changing size.

Embodiment [21] of the present disclosure relates to the braided cord of Embodiments [18]-[20], wherein the twisted or braided core comprises one or more core strands having changing twist level.

Embodiment [22] of the present disclosure relates to the braided cord of Embodiments [18]-[21], wherein the twisted or braided core comprises at least one shaped strand, which is an untwisted strand having a twist level of less than 1 turn per meter, a cross-sectional aspect ratio of at least 3:1, and changing strand width.

Embodiment [23] of the present disclosure relates to the braided cord of Embodiments [1]-[22], which is a round cord having a circular cross-sectional area with a diameter ranging from 0.023 mm to 6 mm.

Embodiment [24] of the present disclosure relates to a process of producing a braided cord with changing cross-sectional area, the process comprising:
- forming a braided sheath by braiding a plurality of sheath strands along a cord axis;
- optionally forming a core surrounded by the braided sheath; and
- obtaining the braided cord with changing cross-sectional area by one of (a) and (b):
  - (a) with the proviso that the braided cord has no core or has a core optionally with changing cross-sectional area, changing thickness of the braided sheath by at least one mode selected from the group consisting of (i) changing size of one or more sheath strands, (ii) changing twist level of one or more sheath strands, (iii) changing pick count of the braided sheath, and (iv) shaping at least one sheath strand, which is an untwisted strand having a twist level of less than 1 turn per meter, so that the at least one shaped sheath strand has a cross-sectional aspect ratio of at least 3:1 and changing strand width; and (b) with the proviso that the braided sheath has a constant thickness and the braided cord has a core, changing cross-sectional area of the core, wherein the braided cord has a cross-sectional area ranging from 0.0004 mm$^2$ to 30 mm$^2$ and contains one or more sections with a tapering angle ranging from 1° to 60° when observed in one direction along the cord axis.

Embodiment [25] of the present disclosure relates to the process of Embodiment [24], wherein the tapering angle ranges from 5° to 45°.

Embodiment [26] of the present disclosure relates to the process of Embodiments [24] and [25], wherein the cross-sectional area of the braided cord changes at a cross sectional area changing rate of larger than 1% per millimeter.

Embodiment [27] of the present disclosure relates to the process of Embodiments [24]-[26], wherein the braided cord has one tapering end.

Embodiment [28] of the present disclosure relates to the process of Embodiments [24]-[26], wherein the braided cord has two tapering ends.

Embodiment [29] of the present disclosure relates to the process of Embodiments [24]-[28], wherein between two ends of the braided cord, the cord contains an in-between section that has periodic or random cross-sectional area variation so that the in-between section contains one or more protrusions and/or depressions.

Embodiment [30] of the present disclosure relates to the process of Embodiments [24]-[29], wherein the braided cord with changing cross-sectional area is obtained by changing twist level of one or more sheath strands.

Embodiment [31] of the present disclosure relates to the process of Embodiments [24]-[30], wherein the braided cord with changing cross-sectional area is obtained by changing pick count of the braided sheath.

Embodiment [32] of the present disclosure relates to the process of Embodiments [24]-[31], wherein the braided cord with changing cross-sectional area is obtained by shaping at least one sheath strand, which is an untwisted strand having a twist level of less than 1 turn per meter, so that the at least one shaped sheath strand has a cross-sectional aspect ratio of at least 3:1 and changing strand width.

Embodiment [33] of the present disclosure relates to the process of Embodiments [24]-[32], comprising: forming the core surrounded by the braided sheath.

Embodiment [34] of the present disclosure relates to the process of Embodiment [33], wherein the core has changing cross-sectional area.

Embodiment [35] of the present disclosure relates to the process of Embodiments [33] and [34], wherein the core is a twisted or braided core comprising a plurality of core strands.

Embodiment [36] of the present disclosure relates to the process of Embodiment [35], wherein the changing cross-sectional area of the twisted or braided core is obtained by shaping at least one core strand, which is an untwisted strand having a twist level of less than 1 turn per meter, so that the at least one core strand has a cross-sectional aspect ratio of at least 3:1 and changing strand width.

Embodiment [37] of the present disclosure relates to the process of Embodiments [35] and [36], wherein the changing cross-sectional area of the twisted or braided core is obtained by changing size of one or more of the core strands.

Embodiment [38] of the present disclosure relates to the process of Embodiments [35]-[37], wherein the changing cross-sectional area of the twisted or braided core is obtained by changing twist level of one or more of the core strands.

Embodiment [39] of the present disclosure relates to the process of Embodiments [35]-[38], wherein the core is a braided core and the changing cross-sectional area of the braided core is obtained by changing pick count of the braided core.

The foregoing discussion discloses and describes exemplary embodiments of the inventive braided cord described in this application and the preparation thereof. Nothing in the above description is meant to limit the scope of the claims. It will be appreciated by those skilled in the art that various modifications and alternatives could be developed in light of the overall teachings of the disclosure. Accordingly, the particular embodiments and examples disclosed herein are meant to be illustrative only and not limiting of the scope of the invention, which is to be given the full breadth of the appended claims and any and all equivalents thereof.

What is claimed is:

1. A braided cord, comprising:
a braided sheath of sheath strands braided along a cord axis, and
optionally a core surrounded by the braided sheath,
wherein each sheath strand comprises one or more fibers and each fiber comprises one or more filaments; and
wherein
with the proviso that the braided cord is coreless or has a core optionally with changing cross-sectional area, the braided sheath has changing thickness achieved by at least one mode selected from the group consisting of (i) one or more sheath strands having changing size, (ii) one or more sheath strands having changing twist level, and (iii) the braided sheath comprising at least one shaped sheath strand, which is an untwisted strand having a twist level of less than 1 turn per meter, a cross-sectional aspect ratio of at least 3:1, and changing strand width; or
with the proviso that the braided sheath has a constant thickness, the braided cord has a core with changing cross-sectional area
so that the braided cord has changing cross-sectional area with a minimum cross-sectional area being at least 0.0004 mm$^2$ and a maximum cross-sectional area being at most 30 mm$^2$ and the braided cord contains one or more sections tapering along the cord axis at a tapering angle of 1° to 60°.

2. The braided cord of claim 1, wherein the cross-sectional area of the braided cord changes at a cross sectional area changing rate of larger than 1% per millimeter.

3. The braided cord of claim 1, wherein
the sheath strands are braided along the cord axis with a constant pick count of 6 to 3000 unit crossovers per meter of the braided cord or with a changing pick count having a minimum value of at least 6 unit crossovers per meter of the braided cord and a maximum value of at most 3000 unit crossovers per meter of the braided cord, and
each filament in the sheath strands has a linear density of 0.2 denier to 30 denier.

4. The braided cord of claim 1, wherein the braided sheath has changing thickness achieved by the braided sheath comprising one or more sheath strands having changing twist level.

5. The braided cord of claim 1, wherein the braided sheath has changing thickness achieved by the braided sheath comprising at least one shaped sheath strand, which is an untwisted strand having a twist level of less than 1 turn per meter, a cross-sectional aspect ratio of at least 3:1, and changing strand width.

6. The braided cord of claim 1, wherein the braided cord is a coreless cord.

7. A braided cord, comprising:
a braided sheath of sheath strands braided along a cord axis, and
a core surrounded by the braided sheath,
wherein each sheath strand comprises one or more fibers and each fiber comprises one or more filaments; and
wherein
the braided sheath has changing thickness achieved by at least one mode selected from the group consisting of (i) one or more sheath strands having changing size, (ii) one or more sheath strands having changing twist level, and (iii) the braided sheath having changing pick count, and (iv) the braided sheath comprising at least one shaped sheath strand, which is an untwisted strand having a twist level of less than 1 turn per meter, a cross-sectional aspect ratio of at least 3:1, and changing strand width; or
with the proviso that the braided sheath has a constant thickness, the core has changing cross-sectional area
so that the braided cord has changing cross-sectional area with a minimum cross-sectional area being at least 0.0004 mm$^2$ and a maximum cross-sectional area being at most 30 mm$^2$ and the braided cord contains one or more sections tapering along the cord axis at a tapering angle of 1° to 60°.

8. The braided cord of claim 7, wherein the core is a braided core, a knitted core, a twisted core, or a plied core.

9. The braided cord of claim 7, wherein the core is a braided core that comprises core strands braided along the cord axis.

10. The braided cord of claim 9, wherein the braided core has changing pick count so that the braided core has changing cross-sectional area.

11. The braided cord of claim 7, wherein the core has changing cross-sectional area and is a twisted or braided core comprising a plurality of core strands.

12. The braided cord of claim 11, wherein the twisted or braided core comprises one or more core strands having changing size.

13. The braided cord of claim 11, wherein the twisted or braided core comprises one or more core strands having changing twist level.

14. The braided cord of claim 11, wherein the twisted or braided core comprises at least one shaped strand, which is an untwisted strand having a twist level of less than 1 turn per meter, a cross-sectional aspect ratio of at least 3:1, and changing strand width.

15. The braided cord of claim 7, wherein the cross-sectional area of the braided cord changes at a cross sectional area changing rate of larger than 1% per millimeter.

16. The braided cord of claim 7, wherein
the sheath strands are braided along the cord axis with a constant pick count of 6 to 3000 unit crossovers per meter of the braided cord or with a changing pick count having a minimum value of at least 6 unit crossovers per meter of the braided cord and a maximum value of at most 3000 unit crossovers per meter of the braided cord, and
each filament in the sheath strands has a linear density of 0.2 denier to 30 denier.

17. A process of producing a braided cord with changing cross-sectional area, the process comprising:
forming a braided sheath by braiding a plurality of sheath strands along a cord axis;
optionally forming a core surrounded by the braided sheath; and
obtaining the braided cord with changing cross-sectional area by one of (a) and (b):
(a) with the proviso that the braided cord has no core or has a core optionally with changing cross-sectional area, changing thickness of the braided sheath by at least one mode selected from the group consisting of (i) changing size of one or more sheath strands, (ii) changing twist level of one or more sheath strands, and (iii) (iv) shaping at least one sheath strand, which is an untwisted strand having a twist level of less than 1 turn per meter, so that the at least one shaped sheath strand has a cross-sectional aspect ratio of at least 3:1 and changing strand width; and
(b) with the proviso that the braided sheath has a constant thickness and the braided cord has a core, changing cross-sectional area of the core,
wherein
each sheath strand comprises one or more fibers and each fiber comprises one or more filaments, and
the braided cord has a minimum cross-sectional area of at least 0.0004 mm$^2$ and a maximum cross-sectional area of at most 30 mm$^2$ and contains one or more sections tapering along the cord axis at a tapering angle of 1° to 60°.

18. The process of claim 17, wherein the cross-sectional area of the braided cord changes at a cross sectional area changing rate of larger than 1% per millimeter.

19. The process of claim 17, wherein
the sheath strands are braided along the cord axis with a constant pick count of 6 to 3000 unit crossovers per meter of the braided cord or with a changing pick count having a minimum value of at least 6 unit crossovers per meter of the braided cord and a maximum value of at most 3000 unit crossovers per meter of the braided cord, and
each filament in the sheath strands has a linear density of 0.2 denier to 30 denier.

20. The process of claim 17, wherein the braided cord with changing cross-sectional area is obtained by changing twist level of one or more of the sheath strands.

21. The process of claim 17, wherein the braided cord with changing cross-sectional area is obtained by shaping at least one sheath strand, which is an untwisted strand having a twist level of less than 1 turn per meter, so that the at least one shaped sheath strand has a cross-sectional aspect ratio of at least 3:1 and changing strand width.

* * * * *